United States Patent [19]

Ginn et al.

[11] Patent Number: 5,458,584
[45] Date of Patent: Oct. 17, 1995

[54] INTRAVASCULAR CATHETER HAVING AN ENCLOSED PROXIMAL END AND A REDUCED PROFILE DISTAL REGION

[75] Inventors: Richard Ginn, San Jose; Yue-Teh Jang, Fremont, both of Calif.

[73] Assignee: Cardiovascular Imaging Systems, Inc., Sunnyvale, Calif.

[21] Appl. No.: 183,458

[22] Filed: Jan. 18, 1994

Related U.S. Application Data

[63] Continuation-in-part of Ser. No. 976,228, Nov. 13, 1992, Pat. No. 5,314,408.

[51] Int. Cl.$^6$ .......................... A61M 5/178; A61M 25/00
[52] U.S. Cl. ........................... 604/280; 604/164; 604/53
[58] Field of Search ................................. 604/280, 284, 604/264, 164, 49, 53

[56] References Cited

U.S. PATENT DOCUMENTS

| | | |
|---|---|---|
| 4,217,904 | 8/1980 | Zahorsky . |
| 4,552,554 | 11/1985 | Gould et al. ............................ 604/280 |
| 4,735,606 | 4/1988 | Davison . |
| 4,748,982 | 6/1988 | Horzewski et al. . |
| 4,772,268 | 9/1988 | Bates . |
| 4,794,931 | 1/1989 | Yock . |
| 4,842,582 | 6/1989 | Mahurkar . |
| 4,936,845 | 6/1990 | Stevens . |
| 4,961,809 | 10/1990 | Marin . |
| 4,994,067 | 2/1991 | Summers . |
| 5,024,234 | 6/1991 | Leary et al. ........................ 128/663.01 |
| 5,054,492 | 10/1991 | Scribner et al. ................... 128/662.06 |
| 5,057,073 | 10/1991 | Martin . |
| 5,078,723 | 1/1992 | Dance et al. . |
| 5,084,010 | 1/1992 | Plaia et al. . |
| 5,135,483 | 8/1992 | Wagner et al. . |
| 5,149,330 | 9/1992 | Brightbill ............................. 604/280 |
| 5,211,627 | 5/1993 | Willian ..................................... 604/82 |
| 5,219,335 | 6/1993 | Willard et al. . |

FOREIGN PATENT DOCUMENTS

| | | | |
|---|---|---|---|
| 242051 | 10/1987 | European Pat. Off. ............... 604/280 |
| 494806 | 7/1992 | European Pat. Off. ............... 604/280 |

OTHER PUBLICATIONS

Endosonics Corporation, Rancho Cordova, Calif. CathScanner I System.
InterTherapy, Costa Mesa, Calif., InterTherapy Modular System Design.
Diasonics, Milpitas, Calif., Interventional Ultrasound System.

*Primary Examiner*—John G. Weiss
*Attorney, Agent, or Firm*—Townsend and Townsend and Crew

[57] ABSTRACT

The present invention provides improvement usable with an intravascular catheter having a single common distal lumen with a reduced profile connected to two or more proximal lumens. The catheter will be loadable over a guidewire into a region of interest within a patient's vascular system. According to one aspect of the present invention, means are provided to ensure that the guidewire enters into a desired one of the proximal lumens. In a preferred embodiment, a special tool is provided to achieve this. According to a second aspect of the present invention, the catheter is provided with a proximal housing and an axially expandable member to shield the rotating parts at the proximal end of the catheter and to allow for convenient movement of a work element within the catheter body.

22 Claims, 8 Drawing Sheets

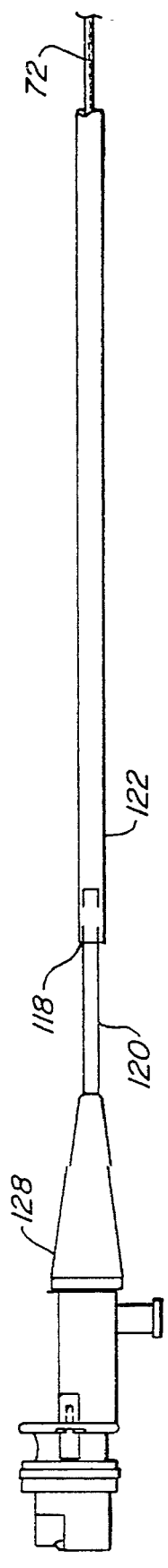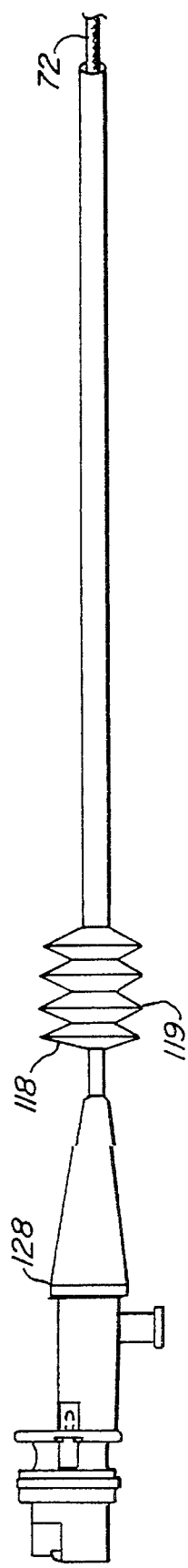

INTRAVASCULAR CATHETER HAVING AN ENCLOSED PROXIMAL END AND A REDUCED PROFILE DISTAL REGION

The present application is a continuation-in-part of application Ser. No. 07/976,228, filed on Nov. 13, 1992 now U.S. Pat. No. 5,314,408. The present application contains subject matter related to that of Ser. No. 07/975,769 and 07/975,752, both filed on Nov. 13, 1992. The disclosures of each of these three applications are incorporated herein by reference.

BACKGROUND OF THE INVENTION

1. Field of the Invention

The present invention relates generally to the construction and use of vascular catheters and, more particularly, to vascular catheters having a reduced-size distal tip capable of selectively receiving either a movable guidewire or a work element.

2. Description of the Background Art

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed limbs of the body and coronary blood vessels that feed the heart. When deposits accumulate in localized regions of the blood vessels, blood flow is restricted and the person's health is at serious risk.

Numerous approaches for reducing and removing such vascular deposits have been proposed, including balloon angioplasty, where a balloon-tipped catheter is used to dilate a stenosed region within the blood vessel; atherectomy, where a blade or other cutting element is used to sever and remove the stenotic material; laser angioplasty, where laser energy is used to ablate at least a portion of the stenotic material; and the like.

In order to more effectively apply such intervention techniques, a variety of vascular imaging devices and methods may be employed. Of particular interest to the present invention, intraluminal imaging catheters having ultrasonic transducers at their distal ends have been employed to produce images of the stenotic region from within the blood vessel.

A number of designs for ultrasonic imaging catheters have been proposed. One approach has been to use a phased-array of discrete ultrasonic imaging transducers at the tip of a vascular catheter. While this approach is advantageous in that it does not require mechanical manipulation of the transducers, it is problematic in that the image quality is limited. Such a phased-array intravascular imaging catheter is commercially available from EndoSonics Corporation, Rancho Cordova, Calif., as the CathScanner I System.

A more promising approach for intravascular ultrasonic imaging employs mechanical rotation of the ultrasonic signal, either by mechanically rotating the transducer itself or by mechanically rotating a mirror, which radially deflects the ultrasonic signal from the transducer. Mechanical rotation generally provides better image quality than use of a phased-array system, but the design of such catheters is problematic since the designs must provide for rotating the transducer and/or an associated mirror at speeds usually in the range from 500 to 2000 rpm. Moreover, the interior blood vessel must be protected from the rotating components, which could cause substantial injury should they come in contact with the blood vessel.

A number of specific designs for mechanical ultrasonic imaging catheters have been described. An early design is illustrated in U.S. Pat. No. 4,794,931, where the mechanical components of the imaging system are located within a housing at the distal end of the catheter. The housing includes a fixed guidewire at its distal tip which is used to position the catheter within the vascular system. While the use of such fixed-guidewire designs can provide excellent image quality, under some circumstances it is desirable to use an "over-the-wire" design where the catheter may be introduced over a separate (movable) guidewire. The use of a movable guidewire offers certain advantages including improved steering capability through branch coronary arteries and elsewhere and easier catheter exchange, e.g. substitution of an interventional catheter after imaging has been completed.

A particular design for an over-the-wire ultrasonic imaging catheter is illustrated in FIG. 1. The catheter includes the catheter body 10 having an exterior catheter lumen 12 attached near its distal end. A rotatable ultrasonic imaging assembly 14 is mounted at the distal end of the drive member 16, and the device may be introduced over a conventional movable guidewire 18, as illustrated. Designs employing parallel lumens are disadvantageous, however, since the width of the distal tip must be sufficient to accommodate both the ultrasonic imaging element and the guidewire. To be able to cross very narrow lesions, the diameter of the catheter should be as small as possible at the distal end. Ideally, the diameter of the catheter in the region of the rotating imaging element should be minimized, preferably including only the imaging element surrounded by a catheter sheath. The requirement of the separate guidewire lumen increases the minimum size, making this design unsuitable for treatment of small blood vessel lesions and preventing passage through conventional guiding catheters.

Designs of the type illustrated in FIG. 1 are commercially available from Medi-Tech, Inc., Watertown, Mass. A design similar to that of FIG. 1 is illustrated in U.S. Pat. No. 5,024,234, the disclosure of which is incorporated herein by reference.

An alternative design for a mechanical ultrasonic imaging catheter avoids the need for a parallel guidewire lumen by providing for exchange of the mechanical imaging components with a conventional guidewire. As illustrated in FIG. 2, such a catheter comprises a single lumen catheter sheath 20 which can receive a drive wire 22 carrying an ultrasonic imaging assembly 24 at its distal end. The catheter sheath 20 may be initially introduced over a conventional guidewire. The guidewire may then be completely removed and replaced with the imaging assembly. While the diameter of the catheter 20 is minimized, the need to exchange the guidewire and imaging components whenever the catheter is to be repositioned is time consuming and disadvantageous. Such catheters are commercially available from Inter-Therapy, Inc., Costa Mesa, Calif.

For these reasons, it is desirable to provide ultrasonic imaging catheters which have a narrow profile in the distal region and which can be introduced over a separate, movable guidewire. It is particularly desirable for such designs to allow for imaging within the narrow distal region of the catheter without the need to remove the guidewire entirely from the catheter body. In particular, such an imaging catheter should present a width of less than about 5 French, and more preferably less than about 3 French, to facilitate entry into the coronary arteries and even very tight lesions.

An imaging catheter of the type having a reduced profile distal region is the subject of co-pending U.S. patent application Ser. No. 07/930,977, the disclosure of which is incorporated herein by reference. Such a catheter is illustrated in FIG. 3. This catheter 50 includes a flexible catheter body 52 having a distal region 54 and a proximal region 56. The distal region 54 includes a single common lumen 58, which extends from a distal port 60 to a transition region 62. The proximal region 56 includes a first lumen 64 and second lumen 66. The first lumen 64 carries a movable guidewire 68 which, as illustrated, extends from a proximal port 70 through the common lumen 58 and in distal region 54 and out the distal port 60.

Catheter 50 further includes a proximal housing 80 secured to the proximal end of the catheter body 52. Proximal housing 80 includes a lever 82, which is attached to the drive shaft 72, which permits the user to selectively reciprocate the ultrasonic imaging assembly 74 between a retracted position and an extended position. The ultrasonic imaging assembly 74 would normally be utilized only when it is in its extended configuration. It will be retracted when the catheter 50 is being positioned over the movable guidewire 68.

The housing 80 further includes an electrical connector plug 84 for coupling the electrical leads on the drive shaft 72 to the necessary electrical instrumentation for producing the ultrasonic image and a spindle 86 at the proximal terminal end of the drive shaft 72 for coupling to a motor drive, as described hereinabove. Conveniently, rings and commutators (not shown) may be provided in a conventional arrangement to couple electrical leads (not shown) from the transducer (running along or through the drive shaft 72) to the connector plug 84.

The steps for inserting a catheter having a common distal lumen into a blood vessel are illustrated in FIGS. 4-6. Initially, a guidewire 68 is fed into the blood vessel BV so that the distal end lies beyond the region of stenosis S, as illustrated in FIG. 4. After positioning of the guidewire 68, the catheter 50 is introduced over the guidewire by passing the proximal end of the guidewire 68 through distal port 60 and subsequently threading the guidewire through common lumen 58 of distal region 54 and lumen 64 in proximal region 56. The catheter is advanced axially forward within the blood vessel until the proximal region 54 lies within the region of stenosis. After the catheter 50 has been properly positioned, the ultrasonic imaging assembly 74 may be advanced to the position shown in FIG. 5 (or alternatively it may have been in such position while the catheter was being introduced to the blood vessel). After imaging assembly 74 is located near the distal end of lumen 66, guidewire 68 will be retracted in the distal direction until it is removed from common lumen 58 in the distal region and lies wholly within lumen 64 within proximal region 56. Once common lumen 58 is cleared of guidewire 68, ultrasonic imaging assembly 74 may be advanced axially forward into common lumen 58, where it can then be used for imaging in a conventional manner.

At any time during the imaging procedure, the drive shaft 72 can be retracted to once again clear common lumen 58. After clearing the lumen, the guidewire can again be advanced axially forward so that it is available for repositioning the catheter 50. Alternatively, guidewire 68 may be left in place and the catheter 50 withdrawn over the guidewire so that it remains in place for different catheters to be introduced.

Catheters having a reduced profile distal region offer significant advantages over those previously available. The reduced profile distal region allows for entry into narrow and tortuous regions of a patient's vascular system. Additionally, the presence of two lumens in the proximal region allows for quicker and easier repositioning of the catheter.

However, catheters of this type can be improved further. When inserting a catheter as shown in FIG. 3 into a blood vessel over the guidewire, the guidewire may advance into the wrong lumen in the proximal region, i.e., into the lumen containing the imaging core. It would be desirable to provide some means for directing the guidewire into the appropriate lumen.

Second, it would be desirable to seal the catheter at its proximal end and to provide a means for convenient advancement and retraction of the imaging core or other work element within the catheter body. This would be doubly advantageous in that it would prevent the entry of foreign or infectious material into the patient from the proximal end and also shield the rotating parts of the catheter at that end. Such a proximal end seal and means for advancing the work element would be applicable not only to catheters having a reduced profile distal end, but other types of catheters as well.

Finally, although co-pending U.S. patent application Ser. No. 07/930,977 speaks only in terms of imaging, there is no reason why use of the refinements of the present invention should be so limited. The improvements of the present invention could also be included in catheters which use balloon angioplasty devices, laser ablation devices, mechanical cutters, or other interventional devices as an alternative or in addition to an imaging device.

SUMMARY OF THE INVENTION

One aspect of the present invention provides an improvement to catheters of the type comprising a catheter body having a common distal lumen and a reduced distal profile. A proximal region of the catheter body includes at least two lumens connected to and in communication with the common distal lumen, with at least one of the lumens being suitable for receiving a movable guidewire and another of the lumens being suitable for receiving an imaging or interventional device, e.g., a rotatable drive shaft having an ultrasonic transducer at its distal end. In this first aspect of the present invention, a means is provided for ensuring that a guidewire travels into the proper lumen as the catheter is positioned over the guidewire.

In a second aspect of the present invention, an improved catheter includes a proximal housing covering the proximal end of the rotating drive shaft and connectable to a motor drive unit. Both aspects of the present invention will be usable with catheters having imaging or interventional devices as work elements.

Various means may be provided to ensure that the guidewire is directed into the proper guidewire lumen. In a particular embodiment, a special tool is inserted through the exterior wall of the guidewire lumen and some distance into the common lumen. This tool can be used to direct the guidewire away from the work element lumen and into the guidewire lumen. Alternative embodiments modify the construction of the catheter to achieve a similar result. For example, the catheter may be preferentially bent or aligned so that the guidewire tends to travel into the guidewire lumen. Additionally, the catheter may be constructed with a gate adapted to close off the work element lumen and deflect the guidewire into the guidewire lumen. The work element itself may also be provided with a tip shaped to deflect the guidewire away from the work element and into the guidewire lumen. A preferred embodiment comprises a visible marker formed on or in the catheter body at or near the transition between the common lumen and the proximal lumens. The marker is aligned with an entry port from the common lumen into one of the proximal lumens and facilitates introduction of the guidewire into the proper lumen.

According to the second aspect of the present invention, a catheter having a drive shaft will be provided with a proximal housing to cover and guard the drive shaft. The proximal housing will also be configured to facilitate connection of the drive shaft to a drive motor at the proximal end of the catheter. In preferred embodiments, this proximal housing will be connected to an axially expandable member extending between the proximal housing and the proximal end of the catheter body with the drive shaft running through the expandable member. Expansion and contraction of the expandable member will allow for convenient advancement and retraction of the work element within the common lumen of the distal region. In a particularly preferred embodiment the expandable member will comprise a pair of cylindrical shafts in overlapping, coaxial (telescopic) engagement with one another. Alternatively, the expandable member may comprise a bellows or similar arrangement.

BRIEF DESCRIPTION OF THE DRAWINGS

FIG. 11A is a side view of a preferred embodiment of the present invention having a proximal housing and a telescoping region for moving the proximal housing with respect to the distal end of the catheter body.

FIG. 11B is a side view of an alternate embodiment of the present invention having a proximal housing and a bellows member for moving the motor housing with respect to the distal end of the catheter body.

DESCRIPTION OF SPECIFIC EMBODIMENTS

Figure 1:
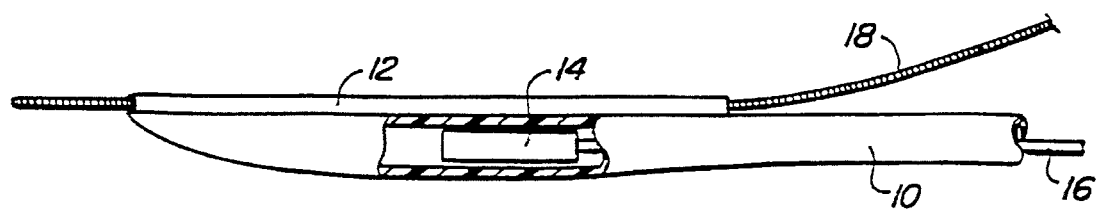
FIG. 1 is a partial sectional view of a prior art imaging catheter having two parallel lumens.
Figure 2:
FIG. 2 is a partial sectional view of a prior art catheter using only one lumen running its full length.
Figure 3:
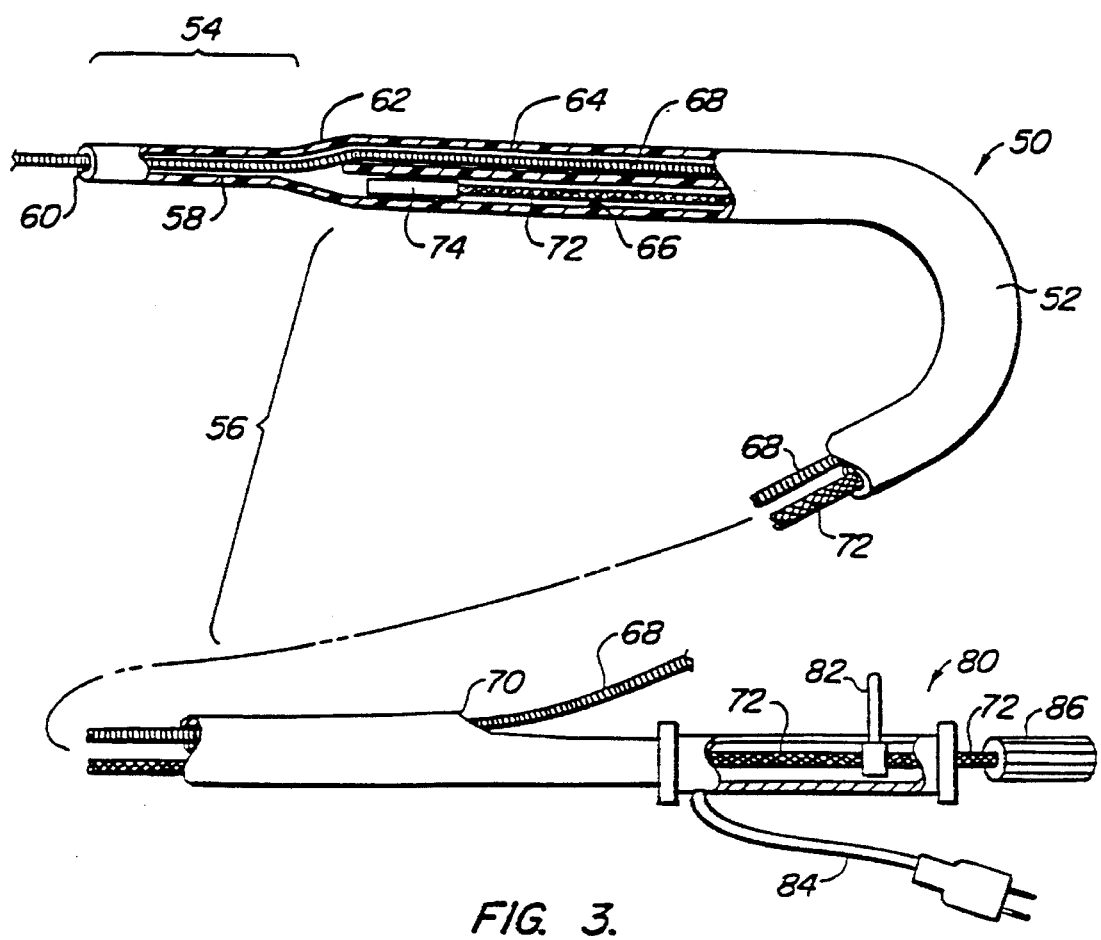
FIG. 3 is a partial sectional view of a catheter having a common distal region with a reduced profile and a proximal region having two or more lumens.
Figure 4:
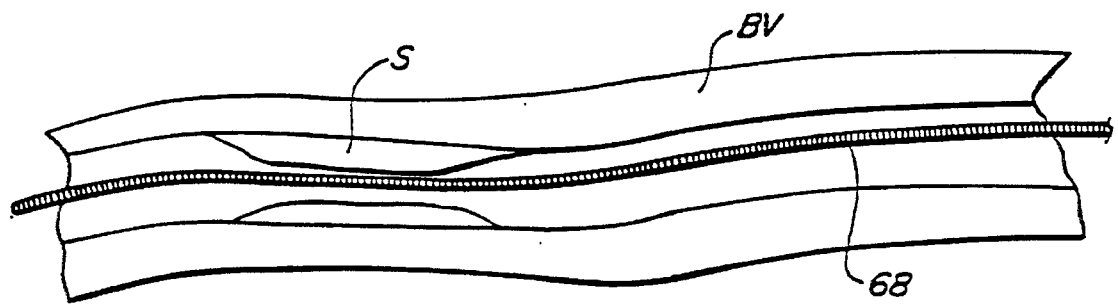
FIG. 4 is a side sectional view of a blood vessel having a stenosed lesion and a guide wire inserted therethrough.
Figure 5:
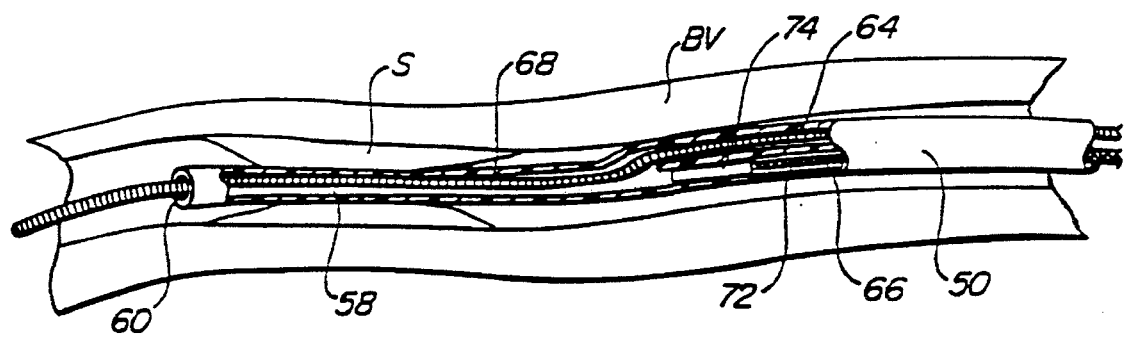
FIG. 5 is a side sectional view of the catheter depicted in FIG. 3 inserted into the blood vessel of FIG. 4.
Figure 6:
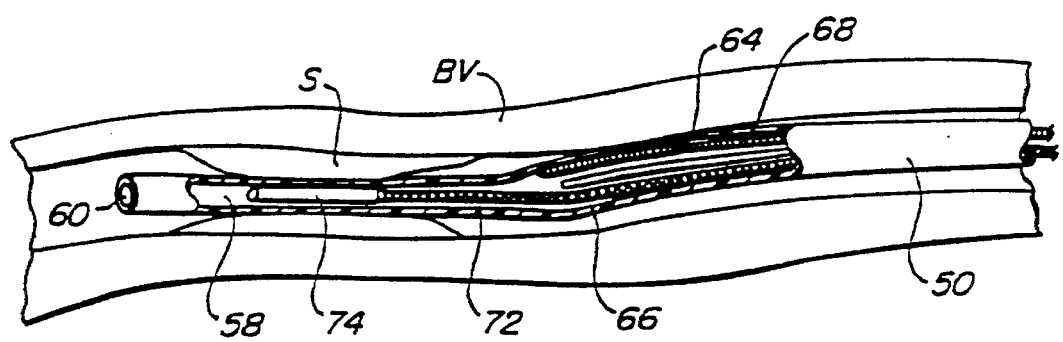
FIG. 6 is a side sectional view of the catheter of FIG. 5 with the guidewire withdrawn into the proximal region and the work element extended into the common lumen.

One aspect of the present invention provides an improvement to catheters having a reduced profile distal region. Such a catheter will comprise an elongate catheter body having a proximal end and a distal end. The catheter body will include at least two regions, a distal region and a proximal region. The distal region will extend from the distal end of the catheter body to a location spaced proximally from the tip. The proximal region will extend proximally from the proximal end of the distal region.

The distal region will have a common lumen extending through it and a reduced cross-sectional area to facilitate entry into coronary blood vessels and/or tight stenotic lesions. The proximal region will have a somewhat larger cross-sectional area to accommodate at least two lumens, a first lumen capable of receiving a conventional movable guidewire and a second lumen capable of receiving a work element attached to the distal end of a drive shaft. Both the first and second lumens connect to the common lumen in the distal region. A catheter having a reduced profile distal region is described in co-pending U.S. patent application Ser. No. 07/930,977, the disclosure of which is incorporated herein by reference. The work element may be an imaging element such as a rotating ultrasonic transducer or it may be an interventional device such as a balloon angioplasty device, a rotational cutter, or a laser ablation device.

The design and use of ultrasonic imaging transducers are described in U.S. Pat. Nos. 3,938,502; 4,576,177; and 4,794,931; disclosures of which are incorporated herein by reference. Catheters employing interventional tools as work elements are described in U.S. Pat. Nos. 4,648,402; 4,669,469; and 4,631,052, the disclosures of which are incorporated herein by reference.

The catheter body may be introduced into a blood vessel with the guidewire passing through the common lumen of the distal region and a first lumen of the proximal region. After the catheter body is in place, the movable guidewire may be retracted within the first lumen of the distal region and the work element advanced into the common lumen from a second lumen in the proximal region. The cross-sectional area of the distal region is thus minimized since it never has to simultaneously accommodate both the work element and the movable guidewire.

The overall dimensions of the catheter will depend on use, with the length varying widely, typically being between about 40 cm and 150 cm, usually being between about 40 cm and 120 cm for peripheral catheters and being between about 110 cm and 150 cm for coronary catheters. The diameter of the catheter body may also vary widely, with the diameter of the distal region typically being between about 2 F (French) and 3 F, and the diameter of the proximal region typically being about 3 F and 6 F. A particular advantage of the catheter of the present invention is that the distal region may be made very small, with the lower limit on size typically being based on the diameter of the ultrasonic transducer or other work element which is being achieved. As the size of such work elements is further decreased with advancements in the art, it is expected that the diameter of the catheter body of the present invention may be made even smaller.

The catheter body may be composed of a wide variety of biologically compatible materials, typically being made from natural or synthetic polymers such as silicone rubber, natural rubber, polyvinyl chloride, polyurethanes, polyesters, polyethylene, polytetrafluoroethylene (PTFE), and the like. Frequently, the catheter body may be formed as a composite having a reinforcement material incorporated within the elastomeric body in order to enhance strength, flexibility, and toughness. Suitable enforcement layers include wire mesh layers. The flexible tubular members of the catheter body will normally be formed by extrusion, with one or more integral lumens being provided. The catheter diameter can then be modified by heat expansion and shrinkage using conventional techniques. Particular techniques for forming the vascular catheters of the present invention are well described in the patent and medical literature.

The catheter body may be formed from a single tubular member, which extends the entire distance from the proximal end to the distal end, or it may be formed from two or more tubular members which are joined together, either in tandem or in parallel. For catheter bodies formed from a single tubular member, the proximal region will be expanded relative to the distal region and appropriate lumens will be formed in the interiors of the two regions. Alternatively, the distal region in the catheter body may be formed from a single tubular member having a single lumen while the proximal region is formed from a second tubular member having at least two axial lumens. The two regions may then be joined together so that the common lumen and the distal tubular element is contiguous with both the parallel axial lumens and the proximal region. As a second alternative, the catheter body may include a single tubular member having a single axial lumen which extends the entire length from the distal end to the proximal end. The proximal section is formed by securing a second tubular member to the side of the first tubular member and penetrating the first tubular member so that the respective lumens are made contiguous. The distal region of the catheter is that portion which remains forward of the point where the two tubes are joined.

The distal region of the catheter will typically have a length in the range from about 1 cm to 30 cm, more typically being in the range from about 2 cm to 20 cm, with the proximal region extending in the proximal direction from the distal region. The proximal region, however, need not extend the entire distance to the proximal end of the catheter body. It will often be desirable to extend the guidewire lumen formed by the proximal region only a portion of the distance from the distal region back toward the proximal end of the catheter body, typically extending from about 10 cm to 30 cm, more typically extending from 15 cm to 25 cm. In this way, the guidewire lumen can have a "monorail" design which facilitates exchange in the catheter over the guidewire. Such monorail designs are described generally in U.S. Pat. No. 4,748,982, the disclosure of which is incorporated herein by reference.

The width of the distal region will typically be below about 0.15 cm, usually being below about 0.13 cm, and frequently being below about 0.1 cm. The width of the proximal region will typically be above about 0.17 cm, and frequently being above about 0.2 cm. The width, of course, need not be uniform along the entire catheter length and some variation is permitted.

The drive shaft, which is reciprocatably disposed within a lumen in the proximal region of the catheter, will be flexible and suitable for transmitting torque from the proximal end of the catheter to the work element at its distal end. Depending on the application, the drive shaft may be a solid core wire, but will more typically have a braided or counter-wound coil construction. Suitable drive shaft constructions are described in U.S. Pat. No. 5,108,411, the disclosure of which is incorporated herein by reference. In the case of an ultrasonic transducer as the work element, the drive shaft will also carry the necessary electrical leads for connecting the transducer. Other work elements, e.g., laser ablation devices, will require electrical power. When such devices are used, the drive shaft can be used to carry power from an external power supply to the work element.

Catheters according to a second aspect of the present invention will include a proximal housing connected to an axially expandable member at the proximal end of the catheter body. The proximal housing and axially expandable member will cover the proximal end of the drive shaft and provide means for reciprocating the drive shaft axially within the catheter body. In the case of ultrasonic imaging catheters, the housing will also include the necessary electrical connection means for coupling the electrical leads on the drive shaft to the associated electronic imaging producing equipment. Although it is contemplated that such a proximal housing will be most useful in catheters having a reduced profile distal region, this improvement may also be advantageous for other catheters, as well.

Figure 7:
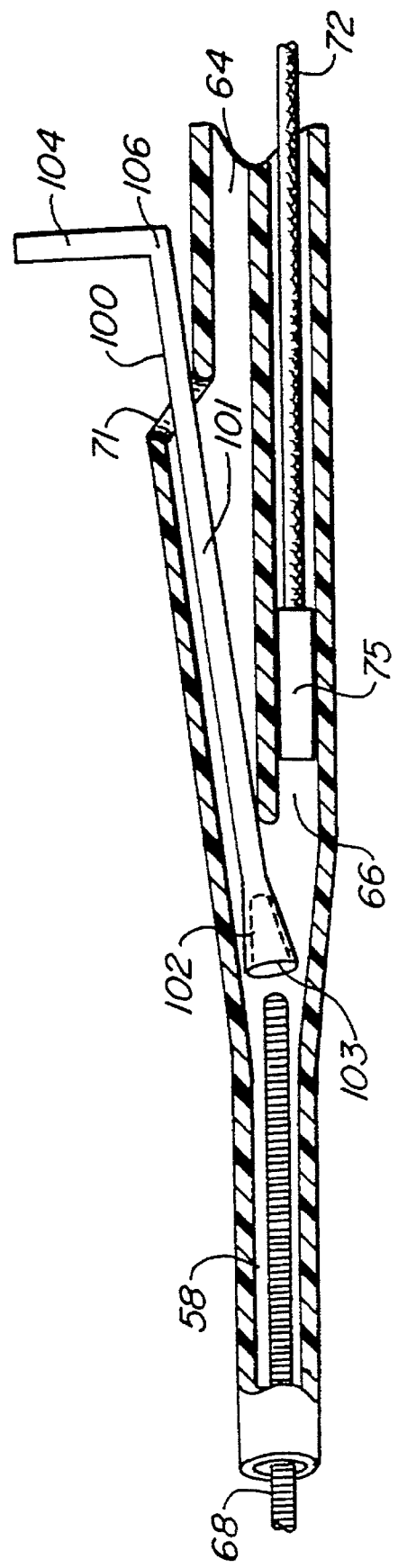
FIG. 7 is a side sectional view of a preferred embodiment of the present invention with a special tool inserted through a lumen of the proximal region and into the common lumen for directing the guidewire into the appropriate lumen.

FIG. 7 depicts a preferred means for ensuring entry of the guidewire into a desired guidewire lumen in a catheter having multiple lumens in its proximal region. A catheter according to this embodiment will be provided with a tool port 71 for insertion of a special tool 100 into guidewire lumen 64 prior to the insertion of guidewire 68 into common lumen 58. Tool 100 has a receiving tip 102 with cavity 103 at one end and grip 104 at the other. Bend 106 is provided to prevent entry of tool 100 either into the catheter or the patient's body.

The catheter body will be sufficiently pliable to allow the insertion of tool 100 into the catheter through tool port 71. The tool should be inserted into the catheter to a point within common lumen 58. After insertion into the common lumen, guidewire 68 will be fed into the catheter until it engages with cavity 103 of receiving tip 102. The tool may then be used to direct the guidewire into guidewire lumen 64 and away from work element lumen 66. Guidewire 68 may be directed as desired either to exit the catheter body through tool port 71 or to travel further along guidewire lumen 64.

Figure 8:
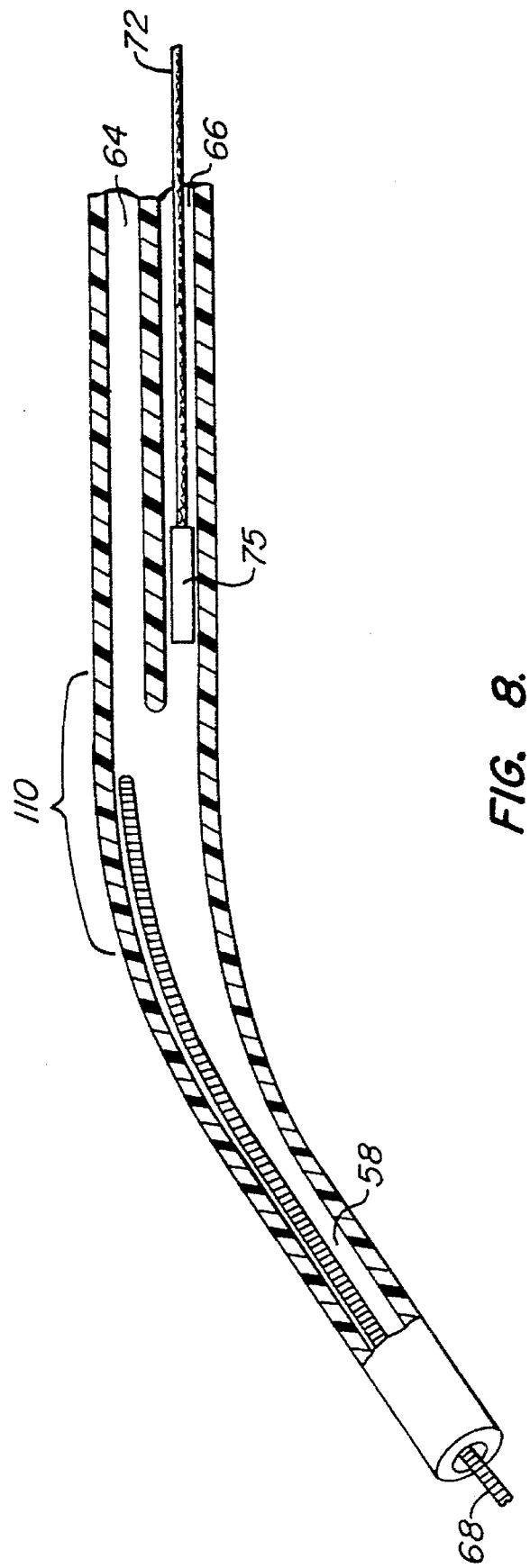
FIG. 8 is a side sectional view of an alternative embodiment of the present invention showing a catheter having a preferential bend for ensuring that the guidewire travels into the appropriate lumen of the proximal region.

FIG. 8 depicts an alternative means for ensuring that guidewire 68 enters guidewire lumen 64 rather than work element lumen 66. In this embodiment, the catheter body is formed with a preferential bend 110 in the transition area between the distal region and the proximal region. The preferential bend is such that guidewire 68 will tend to travel preferentially into the appropriate lumen as the catheter is fed over the guidewire.

Figure 9:
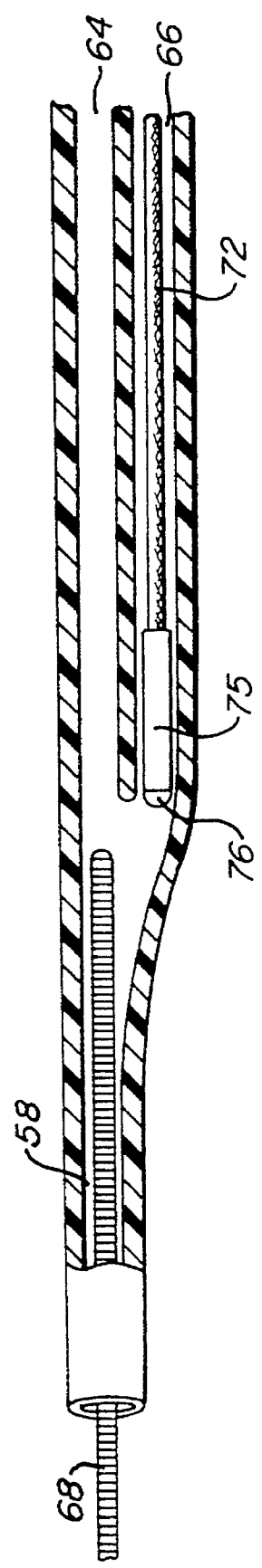
FIG. 9 is a side sectional view depicting an alternative embodiment of the present invention in which the common lumen is aligned parallel to a lumen of the proximal region.

Another embodiment is shown in FIG. 9, which depicts a catheter in which common lumen 58 is preferentially aligned parallel to guidewire lumen 64. This alignment will tend to ensure that guidewire 68 enters guidewire lumen 64. FIG. 9 also shows work element 75 fitted with a deflecting distal tip 76. Distal tip 76 is preferably in the form of a dome or other convex surface to deflect the guidewire away from work element lumen 66 and into guidewire lumen 64. The deflecting distal tip concept may be used alone or in combination with any of the other disclosed means for preventing entry of the guidewire into the work element lumen.

Figure 10:
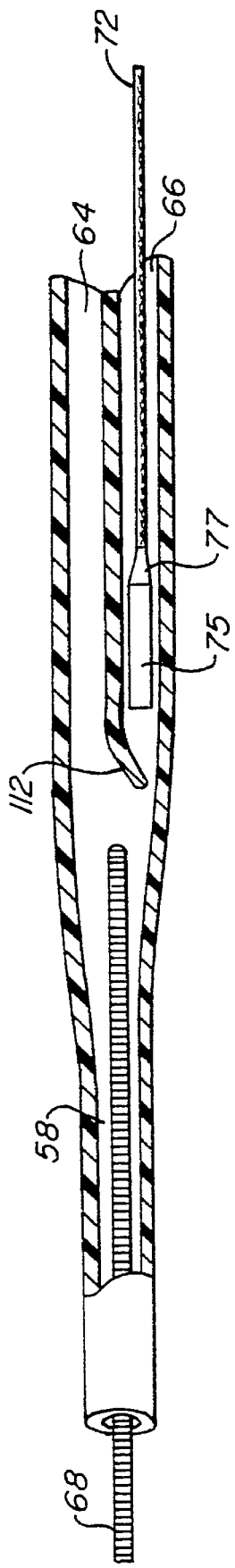
FIG. 10 is a side sectional view depicting an alternative embodiment of the present invention in which the catheter is provided with a gate to close off one of the lumens of the proximal region and deflect the guide wire into another of the lumens.

A further means for directing the guidewire into the appropriate lumen is shown in FIG. 10. In this embodiment, the catheter is provided with a gate 112 at the junction between the distal and proximal regions. Gate 112 is constructed so that it will normally close off work element lumen 66 and deflect guidewire 68 into guidewire lumen 64. Gate 112 is sufficiently flexible, however, so that work element 75 may push it aside in order to advance into common lumen 58. With this embodiment, it may be necessary or desirable to provide work element 75 with a rounded or sloping back surface 77. Back surface 77 should be sloped to assist in pulling work element 75 back through gate 112 and into work element lumen 66 when desired.

Work element 75 will often be an ultrasonic transducer for imaging the interior of the blood vessel. Alternatively, the work element may be an interventional device such as a rotating cutter or laser ablation device for treating the blood vessel. The work element may even be in the form of an interventional device having an angioplasty balloon for reducing the stenosis by dilating the blood vessel. In such a case, the material comprising the common lumen may be made compliant, so that the balloon may be inflated within the common lumen and dilate the blood vessel without exiting the catheter body. The body of the common lumen will simply expand along with the balloon.

Catheters according to a second aspect of the present invention will be provided with a proximal housing and axially expandable member to enclose the rotating drive shaft and to facilitate connection of the drive shaft to a drive motor. A preferred embodiment is depicted in FIG. 11A, which shows proximal housing 128 and expandable member 118 disposed at the proximal end of the catheter system.

Proximal housing 128 encloses the proximal end of drive shaft 72, which is connectable to a motor for rotating work element 75. Proximal housing 128 will also include suitable means for electrically connecting the drive shaft to an imaging means or power source for operating the work element. Means for connecting the power source to the rotatable drive shaft are well known; one such means is described in U.S. Pat. No. 4,794,931, the disclosure of which is incorporated herein by reference.

The catheter of FIG. 11A includes axially expandable member 118, which connects proximal housing 128 to the proximal end of the catheter body. In the exemplary embodiment of FIG. 11A, the expandable member comprises an inner cylindrical member 120, which is secured to the proximal housing, and outer cylindrical member 122, which is defined by the proximal end of the catheter body. Inner member 120 is slidably disposed within outer member 122. By telescoping these two members with respect to one another, the operator may change the effective length of the catheter body. This will result in movement of the work element (axially translated by the drive shaft) between common lumen 58 (see FIG. 7) and work element lumen 66.

Flush port 140 may be used with a hypodermic needle to vigorously inject fluid such as saline solution through the catheter body to clear it of air bubbles in the region of work element 75. This is particularly important if work element 75 is an ultrasonic transducer as trapped air bubbles may interfere substantially with imaging.

Alternatively, axially expandable member 118 may comprise a section of the catheter body in the form of an accordion-like bellows tube 119, as depicted in FIG. 11A. Bellows tube 119 performs the same function as telescoping members 120 and 122 depicted in FIG. 11. As the effective length of the catheter body is changed, work element 75 will be advanced or retracted within the distal end of the catheter body.

The proximal housing and expandable member will be very useful in a catheter having multiple proximal lumens and a common distal lumen. In such a catheter, this improvement will allow for convenient exchange of the work element between the proximal and distal regions. However, the proximal housing and expandable member may find use in other catheter types as well. Such an arrangement provides a cover for the rotating drive shaft at the proximal end while allowing for convenient movement of the work element within the work element lumen.

Figure 12:
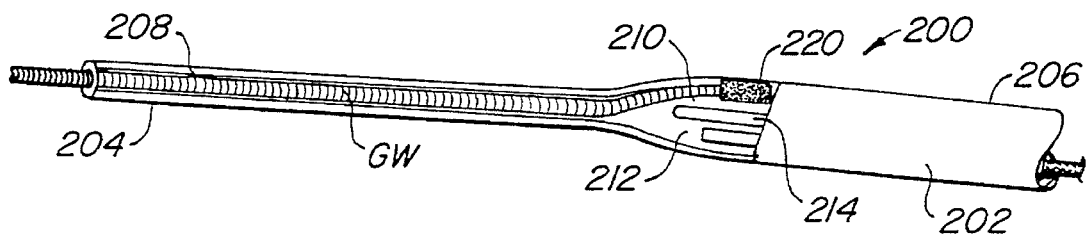
FIG. 12 is a partial sectional view of a catheter having a transparent common lumen and marker aligned with a proximal lumen intended to receive a guidewire.
Figure 13:
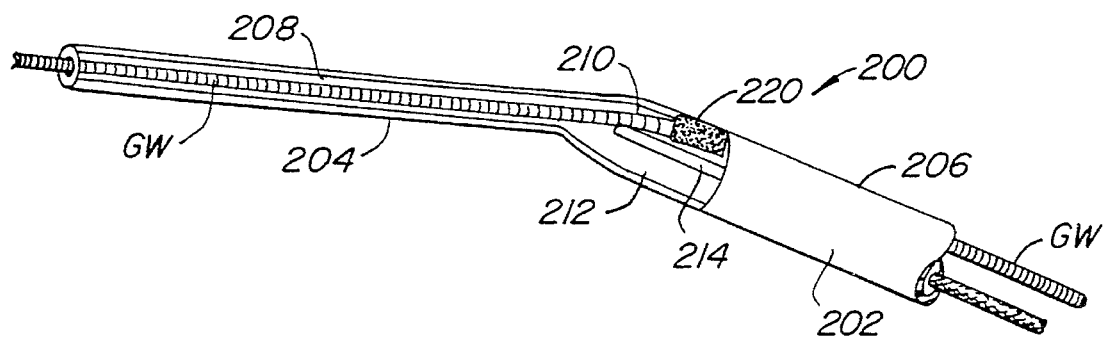
FIG. 13 illustrates the catheter of FIG. 12 being manipulated to selectively advance the guidewire into the marked lumen.

Referring now to FIGS. 12 and 13, an additional and preferred embodiment for the guidewire introducing aspect of the present invention will be described. Catheter 200 comprises catheter body 202 having a distal region 204 and a proximal region 206. Distal region 204 is at least partially transparent (usually being transparent along its entire length) and defines a common lumen 208. Proximal region 206 defines at least two proximal lumens 210 and 212, divided by an intermediate wall 214. Optionally, at least the distal end of the proximal region 206 will also be transparent to permit viewing of the transition region between the distal region 204 and proximal region 206.

According to this preferred aspect of the present invention, a marker 220 will be formed in or on the catheter body 202 at or near the transition region between the distal region 204 and proximal region 206. In particular, the marker 220 will be aligned with one of the proximal lumens 210 and 212, in order to facilitate introduction of a guidewire GW through the common lumen 208 into a selected one of the proximal lumens, as will now be discussed.

As will be appreciated, with very small catheters, it will frequently be difficult to see which of the proximal lumens 210 or 212 the guidewire is being introduced into from the common lumen 208. By providing the visible marker 220, it is much easier for the user to identify the desired target lumen. Once the target lumen is identified, the user can manipulate the catheter 200 so that the guidewire passes into the target lumen. For example, as illustrated in FIG. 14, the catheter body can be bent at or near the region between the distal region 204 and proximal region 206 so that the guidewire preferentially passes into the target lumen adjacent marker 220. Of course, it would be possible to bend the catheter in the opposite direction if it were desired to introduce the guidewire into the other (non-marked) lumen 212. The use of a marker will be advantageous in catheters having two, three, or more, proximal lumens.

In the case where at least the distal end of the proximal region is transparent (as illustrated in FIG. 12), it is not essential that a marker be provided on the catheter body itself. The marker may be a work element or other structure disposed in one of the lumens, indicating to the user that the guidewire is to be inserted through the other, unoccupied lumen. Thus, the present invention includes the use of internal markers within one or more of the proximal lumens to provide visual indication that another of the lumens is to receive the guidewire.

Although the foregoing invention has been described in some detail by way of illustration and example for purposes of clarity of understanding, it will be obvious that certain changes and modifications may be practiced which will still fall within the scope of the appended claims.

What is claimed is:

1. A vascular catheter system comprising:

a catheter body having a proximal end and a distal end, wherein the catheter body includes a proximal region having at least two lumens and a distal region having a common lumen connected to and in communication with both of the lumens of the proximal region and having a cross-sectional area which is less than the combined cross-sectional areas of the two lumens of the proximal region, and wherein one of the two lumens in the proximal region is a guidewire lumen;

a guidewire for insertion into said guidewire lumen; and means for guiding a guidewire into the guidewire lumen as the guidewire is introduced through the distal end of the common lumen and advanced toward the proximal end of the catheter body.

2. The catheter system of claim 1, wherein the common lumen is transparent and the guiding means comprises a marker on the catheter body aligned with the distal end of one of the proximal lumens.

3. The catheter system of claim 1, wherein at least a portion of the proximal region near the distal region is transparent, allowing visual selection of the selected one of the proximal lumens.

4. The catheter system of claim 1, wherein the guiding means comprises a locating tool introducible into one of the lumens of the proximal region for guiding the guidewire from the common lumen into the selected lumen of the proximal region.

5. The catheter system of claim 1, wherein the locating tool has a flared end for receiving a proximal end of the guidewire.

6. The catheter system of claim 1, wherein the guiding means comprises alignment of the common lumen with one of the lumens of the proximal region, whereby the guidewire will tend to enter said one of the lumens of the proximal region when advanced from the common lumen into the proximal region.

7. The catheter system of claim 1, wherein the guiding means comprises a bend in the catheter body at the junction of the proximal and distal regions wherein radially inward and radially outward proximal lumens are defined in the proximal region and the guidewire will tend to enter the radially outward lumen when advanced from the distal region into the proximal region.

8. The catheter system of claim 1, wherein the guiding means comprises a gate disposed at the junction of the proximal and distal regions to direct the guidewire into a selected lumen in the proximal region.

9. The catheter system of claim 1, further comprising:

a drive shaft having a distal end and a proximal end and being reciprocatably disposed in one of the lumens in the proximal region of the catheter body; and a work element secured to the distal end of the drive shaft, whereby the work element may be extended into the single lumen in the distal region or retracted into the lumen in the proximal region by selectively reciprocating the drive shaft.

10. The catheter system of claim 9, wherein the guiding means comprises a distal tip on the work element, the distal tip shaped to deflect the guidewire away from the work element and into a lumen of the proximal region other than that occupied by the work element when the guidewire is fed from the distal region of the catheter body into the proximal region.

11. A method for introducing a guidewire through a catheter having a distal end, a proximal end, a proximal region having at least two lumens and a distal region having a common lumen connected to and in communication with the lumens of the proximal region, the method comprising the steps of:

inserting the guidewire into and through the common lumen of the distal end of the catheter; and guiding the guidewire into a selected lumen of the proximal region.

12. A method as in claim 11, wherein the guiding step comprises viewing the guidewire through a transparent distal region of the catheter and directing the guidewire from the common lumen into one of the proximal lumens designated by the presence or absence of a visible marker aligned with said lumen.

13. A method as in claim 11, wherein the guiding step comprises capturing the distal end of the guidewire with a locating tool introduced into the common lumen from one of the proximal lumens and drawing the guidewire with the tool into said one of the lumens.

14. A method as in claim 11, wherein the guiding step comprises pushing the guidewire straight in the proximal direction into one of said proximal lumens, wherein said one lumen is coaxially aligned with the common lumen.

15. A method as in claim 11, wherein the guiding step comprises pushing the guidewire proximally along a radially outward curved path defined by a bend in the catheter at the transition between the proximal and distal regions, wherein the radially outward curved path is aligned with one of said proximal lumens.

16. A method as in claim 11, wherein the guiding step comprises pushing the guidewire proximally through the common lumen and diverting the distal end of the guidewire in one of the proximal lumens.

17. A method as in claim 16, wherein diverting comprises placing a gate in front of the other lumen or lumens.

18. A method as in claim 16, wherein diverting comprises placing a work element having a deflecting top into the other lumen or lumens.

19. A vascular catheter comprising:

a catheter body having a proximal end and a distal end, wherein the catheter body includes a proximal region having at least two lumens and a distal region having a common lumen connected to and in communication with both of the lumens of the proximal region and having a cross-sectional area which is less than the combined cross-sectional areas of the two proximal lumens, wherein one of the two proximal lumens is a guidewire lumen, and wherein the proximal region is at least partly transparent so that a guidewire is visible as it is introduced proximally toward the proximal lumens.

20. A vascular catheter as in claim 19, further comprising means on the catheter body for visibly marking the distal end of at least one of the proximal lumens so that a user can distinguish between or among the lumens as a guidewire is being inserted through the common lumen into a desired one of said proximal lumens.

21. A vascular catheter as in claim 20, wherein the marking means comprises a color pigment introduced onto or into the catheter body at or near the junction between the distal and proximal regions and aligned with one of said proximal lumens.

22. A vascular catheter as in claim 20, wherein the marking means comprises a colored insert disposed in the catheter body at or near the junction between the distal and proximal regions and aligned with one of said proximal lumens.

* * * * *